US012360086B2

(12) United States Patent
Safai et al.

(10) Patent No.: US 12,360,086 B2
(45) Date of Patent: Jul. 15, 2025

(54) ACTIVE TEMPERATURE COMPENSATION TECHNIQUE FOR STRUCTURAL HEALTH MONITORING SENSORS

(71) Applicant: The Boeing Company, Chicago, IL (US)

(72) Inventors: Morteza Safai, Newcastle, WA (US); Ryan M. Clancy, Saint Charles, MO (US); Kelly A. DeLawder, Bel Air, MD (US)

(73) Assignee: The Boeing Company, Chicago, IL (US)

( * ) Notice: Subject to any disclaimer, the term of this patent is extended or adjusted under 35 U.S.C. 154(b) by 718 days.

(21) Appl. No.: 17/702,513

(22) Filed: Mar. 23, 2022

(65) Prior Publication Data
US 2022/0390418 A1    Dec. 8, 2022

Related U.S. Application Data

(60) Provisional application No. 63/197,792, filed on Jun. 7, 2021.

(51) Int. Cl.
G01N 29/32    (2006.01)
A61B 8/00    (2006.01)
(Continued)

(52) U.S. Cl.
CPC ......... *G01N 29/326* (2013.01); *B06B 1/0622* (2013.01); *G01N 29/04* (2013.01);
(Continued)

(58) Field of Classification Search
CPC ............. G01N 29/326; G01N 29/2437; G01N 29/4463; G01N 29/04; G01N 2291/0289;
(Continued)

(56) References Cited

U.S. PATENT DOCUMENTS

| 4,430,627 A | 2/1984 | Machida |
|---|---|---|
| 5,777,692 A | 7/1998 | Ghosh et al. |

(Continued)

FOREIGN PATENT DOCUMENTS

CN    110596247 A   * 12/2019   ............. G01N 29/04

OTHER PUBLICATIONS

Machine Translation of CN 110596247 (Year: 2019).*

(Continued)

*Primary Examiner* — Kristina M Deherrera
*Assistant Examiner* — Jean F Morello
(74) *Attorney, Agent, or Firm* — Joseph M. Butscher; The Small Patent LAw Group LLC

(57) ABSTRACT

A system and method for detecting an anomaly in a structure using an adaptive filter to compensate for variations in piezoelectric transducer performance due to environmental factors such as temperature. A first voltage signal having a first amplitude is sent to a reference piezoelectric actuator. Thereafter, a first reference voltage signal is received from a reference piezoelectric receiver which is acoustically coupled to detect the guided wave generated by the reference piezoelectric actuator. A second amplitude is determined using an optimization algorithm of an adaptive filter to compensate for nonlinear behavior of the reference piezoelectric actuator and receiver based on the first reference voltage signal. Then the adaptive filter sends a second voltage signal having the second amplitude to the reference and test piezoelectric actuators. Reference and test voltage signals are received from the reference and test piezoelectric receivers in response to the second voltage signal. A difference voltage signal representing differences between the reference and test voltage signals received is then recorded.

20 Claims, 2 Drawing Sheets

(51) Int. Cl.
  *B06B 1/06* (2006.01)
  *G01K 7/20* (2006.01)
  *G01N 29/04* (2006.01)
  *G01N 29/24* (2006.01)
  *G01N 29/44* (2006.01)
  *H03H 11/12* (2006.01)
  *H03H 17/02* (2006.01)
  *H03M 1/06* (2006.01)

(52) U.S. Cl.
  CPC ..... *G01N 29/2437* (2013.01); *G01N 29/4463* (2013.01); *H03H 11/12* (2013.01); *H03H 17/0294* (2013.01); *H03M 1/0626* (2013.01); *A61B 8/546* (2013.01); *G01K 7/20* (2013.01); *G01N 2291/0289* (2013.01); *G01N 2291/106* (2013.01)

(58) Field of Classification Search
  CPC .. G01N 2291/106; G01N 29/11; G01N 29/40; G01N 29/46; G01N 2291/105; G01N 29/346; B06B 1/0622; H03H 17/0294; H03H 11/12; H03M 1/0626; G01K 7/20; A61B 8/546
  USPC .......................................................... 73/602

See application file for complete search history.

(56) References Cited

U.S. PATENT DOCUMENTS

| | | |
|---|---|---|
| 6,757,385 B1 | 6/2004 | Ehrenstrale et al. |
| 7,024,315 B2 * | 4/2006 | Giurgiutiu ............. G01N 29/46 |
| | | 702/33 |
| 7,126,435 B2 | 10/2006 | Naviasky et al. |
| 7,891,247 B2 | 2/2011 | Ihn |
| 8,127,610 B2 | 3/2012 | Mathews |
| 8,745,864 B2 | 6/2014 | Kessler et al. |
| 8,892,384 B2 | 11/2014 | Pado |
| 9,202,453 B2 | 12/2015 | Pan |
| 9,506,836 B2 | 11/2016 | Pado et al. |
| 10,034,092 B1 | 7/2018 | Nawfal et al. |
| 10,126,274 B2 | 11/2018 | Hall et al. |
| 10,562,071 B2 * | 2/2020 | Werlink ................. G01N 29/00 |
| 10,816,436 B2 | 10/2020 | Pado |
| 2023/0064270 A1 * | 3/2023 | Schieke ............... G01N 29/348 |

OTHER PUBLICATIONS

Dan et al., "Temperature Effects Compensation Strategy for Guided Wave Based Structural Health Monitoring", 6th International Symposium on NDT in Aerospace, Nov. 12-14, 2014, Madrid, Spain.
Huang et al., "Adaline Network-Based Temperature Compensation Method for SHM Method", 7th European Workshop on Structural Health Monitoring, Jul. 8-11, 2014, La Cite, Nantes, France, pp 371-378.
Batool et al., "Design and simulation using MATLAB/Simulink on active noise control system for power transformer", EEE 2016 International Conference on Condition Monitoring and Diagnosis (CMD), Xi'an, China, Sep. 25-28, 2016.

* cited by examiner

ACTIVE TEMPERATURE COMPENSATION TECHNIQUE FOR STRUCTURAL HEALTH MONITORING SENSORS

RELATED PATENT APPLICATION

This application claims the benefit, under Title 35, United States Code, Section 119(e), of U.S. Provisional Application No. 63/197,792 filed on Jun. 7, 2021.

BACKGROUND

This disclosure generally relates to the field of structural health monitoring, and more specifically, to systems and methods for providing temperature compensation in a structural health monitoring (SHM) system.

At least some SHM systems have pairs of piezoelectric transducers which are printed on the surface of a structure at separate locations on opposite sides of the region to be monitored. In each pair, one piezoelectric transducer operates as the piezoelectric actuator and the other operates as the piezoelectric receiver. The piezoelectric actuator is activated to generate a vibration signal (e.g., an acoustic wave) that propagates through the monitored region, which propagating signal (e.g., guided wave) is detected by the piezoelectric receiver. Any anomaly along the propagation path affects properties of the guided wave, such as, for example, amplitude and phase. Accordingly, comparing amplitude and phase of a received vibration signal (the comparison signal) at a subsequent time to the amplitude and phase of a previously received vibration signal (the reference signal) enables detection of an anomaly produced in the intervening duration of time. In a properly operating SHM system, the degree of difference between the two signals is proportional to the size of the anomaly. Examples of anomalies include a crack having a length or a delamination area within the structure.

However, propagation of a wave through a structure is also affected by environmental parameters, including, for example, the ambient temperature in the vicinity of the SHM system. Generally, the amplitude of the propagating vibration signal increases with increasing temperature and decreases with decreasing temperature. Ambient temperature can further alter, or shift, the phase of the propagating wave. Such environmental effects can mask an anomaly in the structure, i.e., produce a false-negative, or at least interfere with anomaly detection. Conversely, environmental effects can produce false-positive detection of an anomaly.

Many current SHM sensors are designed to provide a linear signal only in an environment with a constant temperature. These sensors are all linear during testing at constant temperature. There is a large discrepancy in the signal at extreme temperatures. For example, the output amplitude of a piezoelectric transducer drops as the temperature increases. More specifically, the temperature coefficient of a piezoelectric transducer may vary due to ceramic material temperature behavior. The ferroelectric hysteresis decreases with falling temperature. Piezoelectric actuator ferroelectric polarization causes ferroelectric hysteresis. The piezoelectric capacitance effect also depends on temperature. In the range <260° K, the effect decreases with falling temperature by a factor of approximately 0.4% per degree Kelvin. Accordingly, any large variation in temperature inhibits the ability of the SHM system to acquire accurate data during flight. Current SHM systems also do not provide feedback regarding the degradation of the sensor over time.

SUMMARY

The subject matter disclosed below is directed to a structural health monitoring (SHM) system that includes circuitry for compensating for environmental effects (e.g., temperature variations) which degrade sensor performance characteristics. In accordance with one embodiment, the circuitry and active feedback control methodology proposed herein provide temperature compensation for piezoelectric sensors in an embedded SHM system. The technique disclosed herein enables the amplitude of the waveform input to the piezoelectric actuator to be adjusted automatically based on temperature or other environmental factors that introduce nonlinearities into the sensor response.

In accordance with one proposed implementation, the proposed technique uses an adaptive filter which includes an optimization algorithm that adjusts the output of an amplifier (e.g., by adjusting the amplitude of the activation waveform) to compensate for sensor degradation and variations in environmental conditions (e.g., ambient temperature). The adaptive filter includes an adjustable complex digital filter that can be programmed to act as a linear system with a transfer function adapted in accordance with input values of a variable parameter (e.g., as a function of the amplitude of a waveform produced by a reference sensor operating under the same conditions as the test sensor). The adaptive filter further includes circuitry configured to adjust its transfer function in accordance with the outputs of an optimization algorithm.

Key components of the hardware include the following: a Wheatstone bridge resistive temperature sensor system, test piezoelectric actuator and receiver, reference piezoelectric actuator and receiver, two comparators, an adaptive filter feedback control system with optimization algorithm, and a variable gain amplifier power supply which supplies the same waveform with adjusted amplitude to both piezoelectric actuators of reference and test sensors. The adaptive filter is configured to constantly adapt to changing environmental factors in a manner similar to the technique employed in noise-cancelling headphones. Sensor data signals characteristic of nonlinear events (such as temperature-dependent piezo-capacitance) be removed by adaptive filtering. IN accordance with one proposed implementation, sensor data from all sensors may be collected and linear and nonlinear events may be compared for filtering rather than optimizing for just one variable. The system may also be configured to provide the correct bias voltage to enable the system to produce an activation waveform having a temperature-compensated amplitude.

The SHM system disclosed herein is configured to adjust the amplitude of the voltage being supplied to the piezoelectric actuators in a manner which compensates for the variable effects of unknown environmental factors (such a temperature variation) on the performance of the piezoelectric sensors. The feedback loop provides real-time hardware evaluation of sensors to ensure that any deviation in a sensors signal is actually related to a structural anomaly (e.g., a crack) and not some unknown environmental factor.

In accordance with one embodiment, an SHM system with piezoelectric sensors is configured to provide temperature feedback to the adaptive filter. This allows the amplitude of the actuator to be adjusted automatically based on the temperature environment. An adaptive filter is used which includes an optimization algorithm that adjusts amplifier output to compensate for temperature variation. The reference actuator and reference receiver are used to compare actual data with optimization in real time. Signal comparison constantly provides data for the optimization algorithm.

The advantages of the system and method disclosed herein are manifold. The system and method provide better feedback optimization with amplitude control. The reference sensor provides real-time conditioning of the sensor, giving information on the system health, accuracy, and non-linearity. This information will be used to assist the optimization algorithm.

Although various embodiments of systems and methods for adaptive filter-based temperature compensation for SHM sensors will be described in some detail below, one or more of those embodiments may be characterized by one or more of the following aspects.

One aspect of the subject matter disclosed in detail below is a structural health monitoring system comprising: a structure having a surface; first and second piezoelectric transducers arranged on the surface in a first pitch-catch configuration; third and fourth piezoelectric transducers arranged on the surface in a second pitch-catch configuration; a voltage source configured to generate a first voltage signal representing an uncompensated waveform having a first amplitude; an adaptive filter connected to receive digital voltage amplitude samples derived from the first voltage signal, configured to convert the digital voltage amplitude samples to a second voltage signal representing a second waveform having a second amplitude different than the first amplitude, and connected to send the second voltage signal to the first and third piezoelectric transducers; a first comparator connected to receive reference and test voltage signals from the second and fourth piezoelectric transducers respectively subsequent to sending of the second voltage signal, the first comparator being configured to output a difference voltage signal representing differences between the reference and test voltage signals; and an analog-to-digital converter connected to receive the reference voltage signal from the second piezoelectric transducer and configured to convert the reference voltage signal to digital reference voltage amplitude samples. The adaptive filter is further connected to receive the digital reference voltage amplitude samples from the analog-to-digital converter and determine the second amplitude in dependence on the reference digital voltage amplitude samples received from the analog-to-digital converter.

Another aspect of the subject matter disclosed in detail below is a structural health monitoring system comprising: a structure having a surface; first and second piezoelectric transducers arranged on the surface in a first pitch-catch configuration; third and fourth piezoelectric transducers arranged on the surface in a second pitch-catch configuration; a voltage source configured to generate a first voltage signal representing an uncompensated waveform having a first amplitude; voltage biasing circuitry configured to convert the first voltage signal to digital voltage amplitude samples; an adaptive filter configured to adaptively filter the digital voltage amplitude samples and output a second voltage signal representing a second waveform having a second amplitude different than the first amplitude; a first comparator connected to receive reference and test voltage signals from the second and fourth piezoelectric transducers respectively and configured to output a difference voltage signal representing differences between the reference and test voltage signals; and an analog-to-digital converter connected to receive the reference voltage signal from the second piezoelectric transducer and configured to convert the reference voltage signal to digital reference voltage amplitude samples. The adaptive filter is further connected to receive the digital reference voltage amplitude samples from the analog-to-digital converter and further configured to output the second voltage signal representing the compensated waveform in dependence on the reference digital voltage amplitude samples received from the analog-to-digital converter. The first and third piezoelectric transducers are connected to receive the second voltage signal from the adaptive filter and respectively configured to generate reference and test guided waves in first and second portions of the structure in response to receipt of the second voltage signal. The second piezoelectric transducer is configured to sense the first guided wave and output the reference voltage signal having a characteristic dependent on the first guided wave. The fourth piezoelectric transducer is configured to sense the second guided wave and output the test voltage signal having a characteristic dependent on the second guided wave.

A further aspect of the subject matter disclosed in detail below is a method for detecting an anomaly in a structure, the method comprising: (a) sending a first voltage signal having a first amplitude to a reference piezoelectric actuator which is acoustically coupled to generate a guided wave in a structure in response to receipt of the first voltage signal; (b) receiving a reference voltage signal from a reference piezoelectric receiver which is acoustically coupled to detect the guided wave generated by the reference piezoelectric actuator in response to sending the first voltage signal; (c) determining a second amplitude which is optimized to compensate for nonlinear behavior of the reference piezoelectric actuator and reference piezoelectric receiver based on the reference voltage signals; (d) concurrently sending a second voltage signal having a second amplitude to the reference piezoelectric actuator and to a test piezoelectric actuator which is acoustically coupled to generate a guided wave in the structure in response to receipt of the second voltage signal; (e) concurrently receiving reference and test voltage signals from reference and test piezoelectric receivers in response to sending the second voltage signal; (f) outputting a difference voltage signal representing differences between the reference and test voltage signals received in response to sending the second voltage signal; and (g) recording data representing the difference voltage signal in a non-transitory tangible computer-readable storage medium. Steps (a) through (d) are performed by an adaptive filter. In particular, step (c) is performed by an optimization algorithm of the adaptive filter that is configured to adjust amplitude of a voltage signal sent to the reference and test piezoelectric actuators to compensate for variation in piezoelectric transducer performance due to an environmental factor. In accordance with one embodiment, the environmental factor is temperature.

Other aspects of systems and methods for adaptive filter-based temperature compensation for SHM sensors are disclosed below.

BRIEF DESCRIPTION OF THE DRAWINGS

The features, functions and advantages discussed in the preceding section may be achieved independently in various embodiments or may be combined in yet other embodiments. Various embodiments will be hereinafter described with reference to drawings for the purpose of illustrating the above-described and other aspects. None of the diagrams are drawn to scale.

Reference will hereinafter be made to the drawings in which similar elements in different drawings bear the same reference numerals.

DETAILED DESCRIPTION

Figure 1:
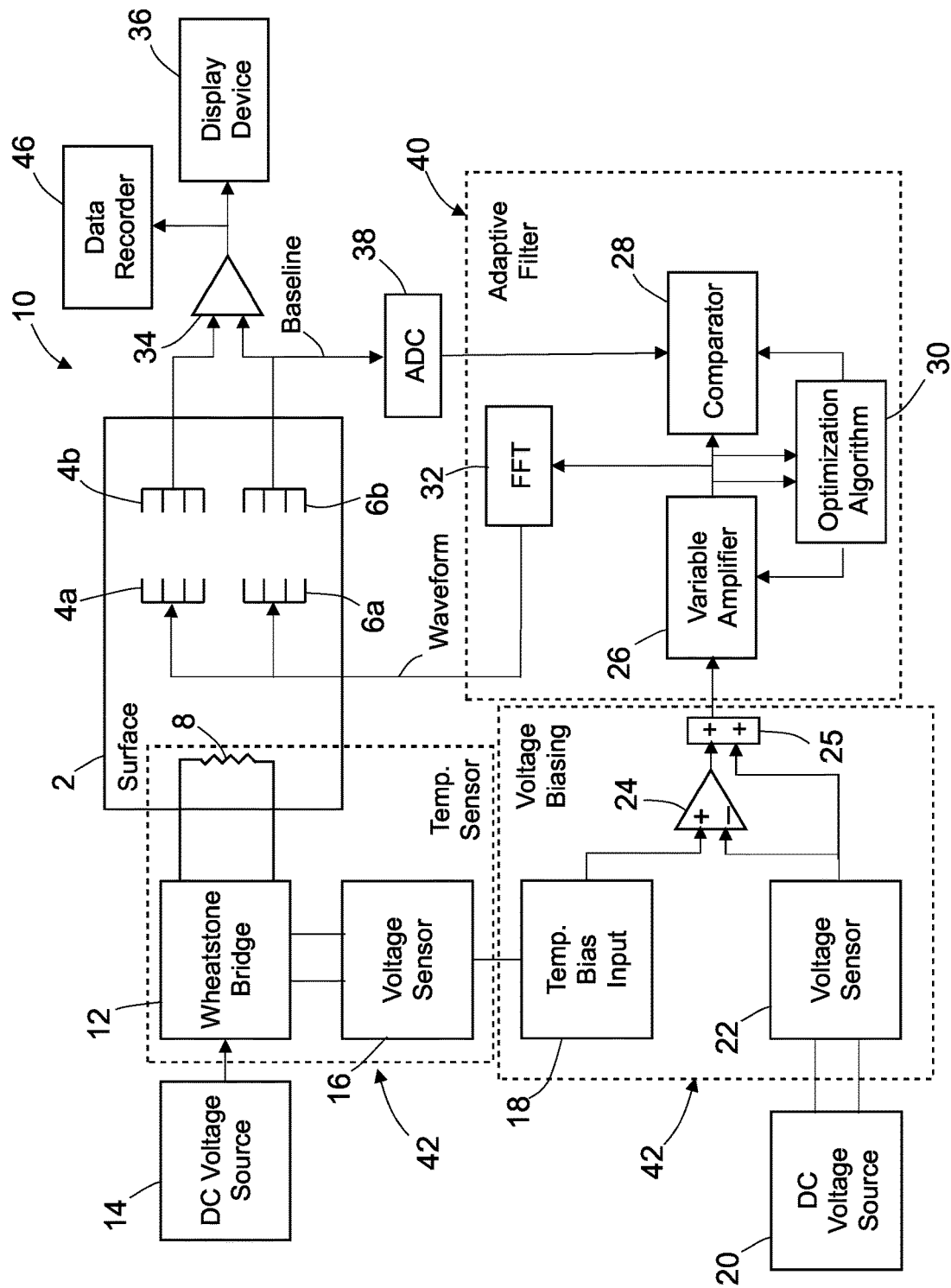
FIG. 1 is a block diagram identifying components of an SHM system including adaptive filter-based temperature compensation for piezoelectric sensors in accordance with one embodiment.

Illustrative embodiments of systems and methods for adaptive filter-based temperature compensation for SHM sensors are described in some detail below. However, not all features of an actual implementation are described in this specification. A person skilled in the art will appreciate that in the development of any such embodiment, numerous implementation-specific decisions must be made to achieve the developers specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

A typical structural health monitoring (SHM) system includes a computer or processor configured (e.g., programmed or hard-wired) that computes a damage index (DI) that enables detection of damage in a structure, such as, for example, an aircraft structure. The typical SHM system further includes a plurality of piezoelectric transducers distributed over an area of a structure and printed on (or bonded to) the surface of the structure. Each actuating transducer is configured to be excited to generate a vibration signal that propagates through the structure and is then received at one or more receiving transducers. As used herein, the term "piezoelectric actuator" means a piezoelectric transducer in an excitation mode (transducing electrical charge into mechanical waves); the term "piezoelectric receiver" means a piezoelectric transducer in a sensing mode (transducing mechanical waves into electrical charge). A piezoelectric actuator first generates a reference vibration signal that propagates through the structure and is received by at least one piezoelectric receiver, collected by a data recorder (e.g., a data acquisition circuit), and stored in a non-transitory tangible computer-readable storage medium. The piezoelectric actuator then later generates a comparison vibration signal that propagates through the structure and is received by the sensor transducer and collected by the data recorder. A processor then computes a DI as a function of an amplitude of the reference vibration signal divided by an amplitude of the comparison vibration signal. Damage that occurs in the duration between the time at which the reference vibration signal is generated and the time at which the comparison vibration signal is generated, is identified when the DI is positive. Each DI value represents a quantification of the health of the structure, e.g., a metal structure or a composite structure, along the path of the guided wave for that DI value. Accordingly, this quantification enables monitoring of the structural health of the structure periodically over time.

The system and methodology proposed herein enhances the performance of piezoelectric transducers in an SHM system by automatically adjusting the amplitude of the exciting signal sent to the piezoelectric actuators based on feedback signals carrying information about the operating environment (e.g., temperature). An adaptive filter including an optimization algorithm is configured to adjust the excitation signal output by a variable-gain amplifier to compensate for variation due to environmental factors such as temperature. A reference actuator and reference receiver are used to compare actual data and determine a residual (a.k.a. error) that is utilized by an optimization algorithm of the adaptive filter in real time. The signal comparison constantly provides data for the optimization algorithm.

FIG. 1 is a block diagram identifying components of an SHM system 10 that includes adaptive filter-based temperature compensation for piezoelectric sensors in accordance with one embodiment. SHM system 10 includes a plurality of piezoelectric transducers printed on or bonded to the surface of a structure 2. In accordance with one proposed implementation, the electric conductors that connect to the electrodes of the piezoelectric transducers may be printed using direct-write (DW) technology. The use of DW technology enables conformal deposition of conductive traces onto a variety of complex surfaces with a high degree of precision. The DW technology may selectively deposit electrically conductive traces with very fine tolerances either directly onto the structure 2 or onto a layer that can be applied to the structure 2. Such conformal DW traces may create a structural component with multifunctional capabilities, increasing instrumentation reliability while greatly reducing weight as compared to a cable-based equivalent. Additionally, the cable-free sensor bus may be flexible or semi-flexible to reduce installation concerns.

The piezoelectric transducers may be arranged on the surface of structure 2 in respective pitch-catch configurations. The piezoelectric transducers depicted in FIG. 1 include a test piezoelectric actuator 4a and a test piezoelectric receiver 4b arranged in a first pitch-catch configuration; and a reference piezoelectric actuator 6a and a reference piezoelectric receiver 6b arranged in a second pitch-catch configuration. The piezoelectric transducers are distributed over an area of structure 2 and arranged for testing structure 2. For aircraft structures, for example, piezoelectric transducers may be arranged such that they are concentrated on high-stress areas of the given aircraft structure, which may be constructed of metal materials or composite materials having multiple layers, or laminations, for example. The piezoelectric transducers may be made of ceramic material, such as lead zirconate titanate.

Still referring to FIG. 1, the SHM system 10 further includes an adaptive filter 40 that provides a temperature-compensated voltage signal for concurrent activation of test piezoelectric actuator 4a and reference piezoelectric actuator 6a. In response to that common activation signal, test piezoelectric actuator 4a and reference piezoelectric actuator 6a generate respective guided waves in structure 2 which are respectively sensed by test piezoelectric receiver 4b and reference piezoelectric receiver 6b. The test piezoelectric receiver 4b outputs a test voltage signal produced by transducing impinging guided waves; the reference piezoelectric receiver 6b outputs a reference voltage signal produced by transducing impinging guided waves.

In summary, the test and reference piezoelectric actuators are connected to receive the temperature-compensated voltage signal from the adaptive filter 40 and respectively configured to generate reference and test guided waves in first and second portions of structure 2 in response to receipt of the temperature-compensated voltage signal. The reference piezoelectric receiver 6b is configured to sense a first guided wave generated by reference piezoelectric actuator 6a and output a reference voltage signal having a characteristic dependent on the first guided wave. Similarly, the test piezoelectric receiver 4b is configured to sense a second guided wave generated by test piezoelectric actuator 4a and output a test voltage signal having a characteristic dependent on the second guided wave.

The SHM system 10 further includes a signal comparator 34 having two inputs and one output. The signal comparator 34 may, for example, be an operational amplifier. The inputs of signal comparator 34 respectively receive the test voltage signal from test piezoelectric receiver 4b and the reference voltage signal from reference piezoelectric receiver 6b. The signal comparator 34 is configured to output a difference voltage signal representing differences between the reference and test voltage signals. The sensor data contained in the difference voltage signal is then collected by a data recorder 46 (e.g., a data acquisition circuit) and displayed on a display device 36. The data recorder 46 includes a non-transitory tangible computer-readable storage medium. The difference voltage signal may be converted to digital values by one or more analog-to-digital converters within the data recorder. Any difference between the reference and test voltage signals may be attributable to the presence of an anomaly in structure 2 in the area intersected by the guided wave which propagates from test piezoelectric actuator 4a to test piezoelectric receiver 4b. The display device 36 is connected to the output of signal comparator 34 and configured to display symbology representing the difference voltage signal.

The SHM system 10 depicted in FIG. 1 further includes a temperature sensor 42 which is thermally coupled to the structure 2 and configured to output a digital temperature value indicating the temperature of structure 2 in proximity to the piezoelectric transducers. The temperature sensor 42 includes a resistance thermometer 8, a Wheatstone bridge 12, and a voltage sensor 16.

The resistance thermometer 8 is thermally coupled to the surface of structure 2. The resistance thermometer 8 is a sensing element constructed of a metal having a repeatable resistance versus temperature relationship and operating temperature range. Thus, a change in the resistance of resistance thermometer 8 indicates a change in the temperature of structure 2. The Wheatstone bridge 12 is connected to the resistance thermometer 8 and to a DC voltage source 14. The Wheatstone bridge 12 is configured to output a DC voltage signal representing a resistance value of the resistance thermometer 8. The voltage sensor 16 is connected to receive the DC voltage signal from the Wheatstone bridge 12. The voltage sensor 16 is configured to convert the DC voltage signal to a digital temperature value.

The SHM system 10 also includes voltage biasing circuitry 44 which is connected to receive the digital temperature value from the temperature sensor 42 and a voltage signal from a DC voltage source 20 (hereinafter "voltage source 20"). The voltage biasing circuitry 44 is configured to bias the voltage signal supplied by voltage source 20, taking into account the digital temperature value received from temperature sensor 42. More specifically, the voltage biasing circuitry is configured to convert the voltage signal from voltage source 20 to digital voltage amplitude samples that include a bias based on the digital temperature value. The voltage biasing circuitry 44 sends the digital voltage amplitude samples to the adaptive filter 40.

In accordance with the proposed implementation depicted in FIG. 1, the voltage biasing circuitry 44 includes a temperature bias input circuit 18, a voltage sensor 22, an operational amplifier 24, and a summer 25. The temperature bias input circuit 18 has an input connected to the output of voltage sensor 16 of temperature sensor 42. The temperature bias input circuit 18 is configured to normalize the digital temperature value to be within a range acceptable to the operational amplifier 24. The voltage sensor 22 has inputs connected to outputs of voltage source 20. The voltage sensor 22 is configured to convert the voltage signal to digital voltage amplitude samples. The operational amplifier 24 has one input connected to the output of temperature bias input circuit 18 and another input connected to the output of voltage sensor 22. The summer has one input connected to the output of operational amplifier 24 and another input connected to the output of voltage sensor 22. The summer 25 sums the inputs from voltage sensor 20 and operational amplifier 24 and outputs digital voltage amplitude samples to the adaptive filter 40.

The voltage source 20 is configured to generate a first voltage signal representing an uncompensated waveform having a first amplitude. The adaptive filter 40 is connected to receive digital voltage amplitude samples derived from the first voltage signal as previously described. The adaptive filter 40 is configured to convert the digital voltage amplitude samples to a second voltage signal representing a second waveform having a second amplitude different than the first amplitude. The adaptive filter 40 is connected to send the second waveform to test piezoelectric actuator 4a and reference piezoelectric actuator 6a. The second amplitude is determined based on feedback from the reference piezoelectric receiver 6b, which is received in digital form via an analog-to-digital converter 38, which is connected to receive the analog reference voltage signal from reference piezoelectric actuator 6a.

Still referring to FIG. 1, the adaptive filter 40 comprises a variable-gain amplifier 26, a comparator 28, a processor or circuitry that executes steps of an optimization algorithm 30, and a fast Fourier transform circuit 32. The variable-gain amplifier 26 is connected to receive the digital unfiltered voltage amplitude samples from summer 25. The variable gain of variable-gain amplifier 26 is determined by the optimization algorithm 30. The processor or circuitry that executes steps of an optimization algorithm 30 sets the gain by sending a control signal to variable-gain amplifier 26. The variable-gain amplifier 26 thus configured to output digital filtered voltage amplitude samples with a gain that is a function of the control signal.

The comparator 28 is connected to receive digital reference voltage amplitude samples from analog-to-digital converter 38 and digital filtered voltage amplitude samples from a variable-gain amplifier 26. The comparator 28 is configured to output difference values (a.k.a. errors) representing respective differences between the digital reference voltage amplitude samples and the digital filtered voltage amplitude samples. The optimization algorithm 30 is configured to output the control signal to the variable-gain amplifier 26 in dependence on the difference values output by the comparator 28.

The adaptive filter 40 further includes fast Fourier transform circuitry 32 which is configured to apply a fast Fourier transform to the digital filtered voltage amplitude samples output by variable-gain amplifier 26. More specifically, fast Fourier transform circuitry 32 converts the digital filtered voltage amplitude samples into the second voltage signal representing a waveform having an amplitude which is different than the amplitude of the voltage supplied by the voltage source 20. The voltage amplitude is adjusted by the optimization algorithm 30 to compensate for discrepancies in the test voltage signal due to environmental factors.

Figure 2:
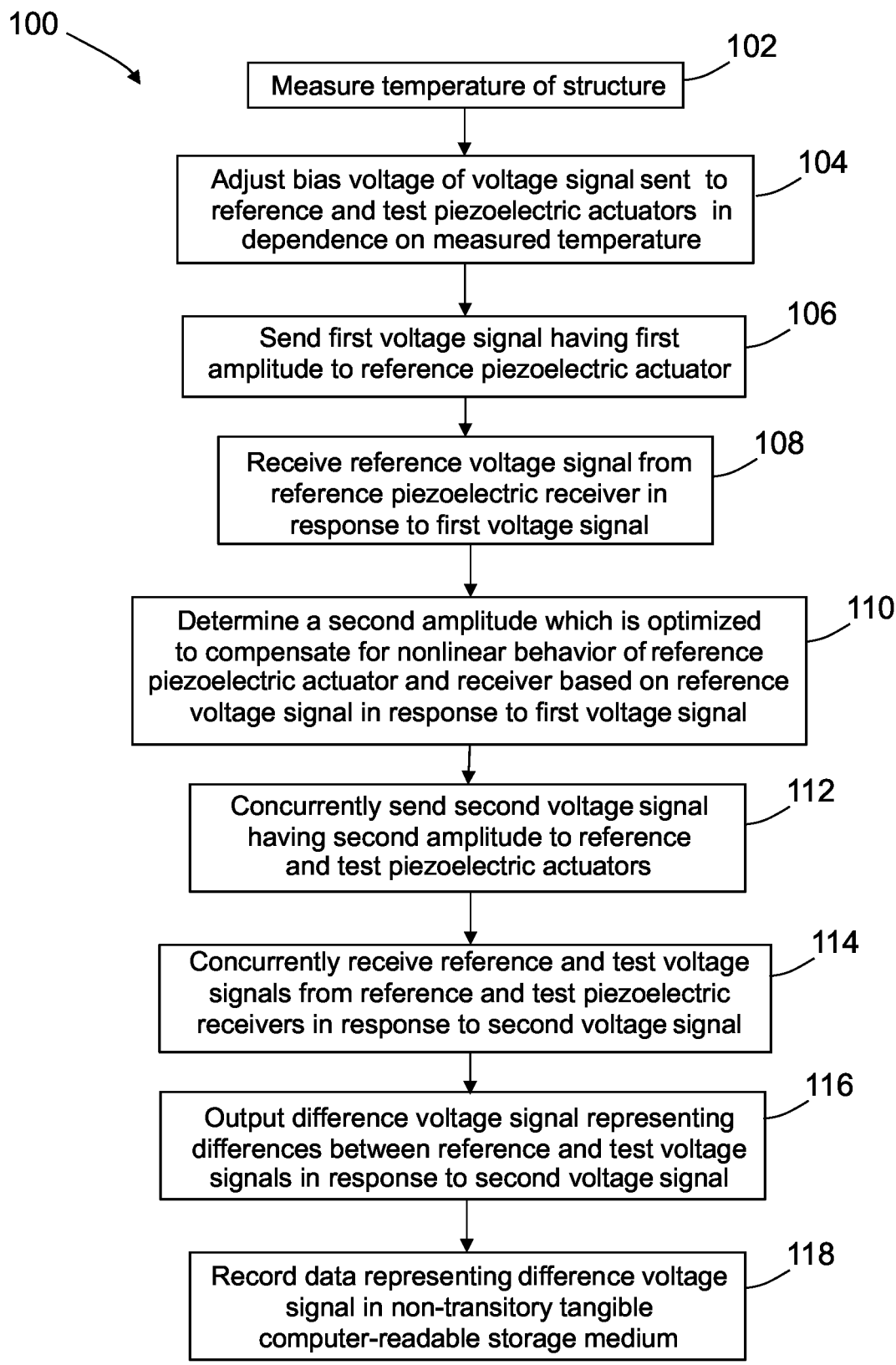
FIG. 2 is a flowchart identifying steps of a method for providing adaptive filter-based temperature compensation for piezoelectric sensors in an SHM system in accordance with one embodiment.

FIG. 2 is a flowchart identifying steps of a method 100 for detecting an anomaly in a structure 2 in accordance with one embodiment. The temperature of structure 2 is measured (step 102). A bias voltage of the voltage signal sent to the reference and test piezoelectric actuators is adjusted in dependence on the measured temperature (step 103). A first voltage signal having a first amplitude is sent to the reference piezoelectric actuator 6a (which is acoustically coupled to generate a guided wave in structure 2) in response to receipt of the first voltage signal (step 106). Thereafter, a reference voltage signal is received from the reference piezoelectric receiver 6b (which is acoustically coupled to detect the guided wave generated by the reference piezoelectric actuator 6a) in response to sending the first voltage signal (step 108). A second amplitude is determined using the optimization algorithm 30 to optimize to compensate for nonlinear behavior of the reference piezoelectric actuator 6a and reference piezoelectric receiver 6b (step 110). Step 110 is performed by an optimization algorithm that is configured to adjust an amplitude of a voltage signal sent to the reference and test piezoelectric actuators to compensate for variation in piezoelectric transducer performance due to an temperature variations. The optimization is based on the reference voltage signals generated by the reference piezoelectric receiver 6b.

Following optimization, a second voltage signal having the second amplitude is sent concurrently to the reference piezoelectric actuator 6a and to the test piezoelectric actuator 4a (step 112). The actuators are acoustically coupled to generate concurrent guided waves in the structure 2 in response to receipt of the second voltage signal. Then the reference and test voltage signals generated by the receivers are concurrently received by the signal comparator 34 (step 114) in response to sending the second voltage signal. The signal comparator 34 outputs a difference voltage signal representing differences between the reference and test voltage signals received in response to sending the second voltage signal (step 116). The data representing the difference voltage signal is then recorded in a non-transitory tangible computer-readable storage medium (step 118), such as data recorder 46.

The flowchart and block diagram illustrate the architecture, functionality, and operation of one possible implementation of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowchart or block diagram.

The structure 2 may be made fiber-reinforced composite material consisting of a plurality of plies or layers, a solid metallic material, or other similar solid or laminated material. The structure 2 may be a vehicle (such as an aerospace vehicle, terrestrial vehicle, or watercraft), public infrastructure (such as a bridge, building or other structure), or any object where monitoring the structural health or condition is desired.

While systems and methods for adaptive filter-based temperature compensation for SHM sensors have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

In the method claims appended hereto, any alphabetic ordering of steps is for the sole purpose of enabling subsequent short-hand references to antecedent steps and not for the purpose of limiting the scope of the claim to require that the method steps be performed in alphabetic order.

The invention claimed is:

1. A structural health monitoring system comprising:
a structure having a surface;
first and second piezoelectric transducers arranged on the surface in a first pitch-catch configuration;
third and fourth piezoelectric transducers arranged on the surface in a second pitch-catch configuration;
a voltage source configured to generate a first voltage signal representing an uncompensated waveform having a first amplitude;
an adaptive filter connected to receive digital voltage amplitude samples derived from the first voltage signal, configured to convert the digital voltage amplitude samples to a second voltage signal representing a second waveform having a second amplitude different than the first amplitude, and connected to send the second voltage signal to the first and third piezoelectric transducers;
a first comparator connected to receive reference and test voltage signals from the second and fourth piezoelectric transducers respectively subsequent to sending of the second voltage signal, the first comparator being configured to output a difference voltage signal representing differences between the reference and test voltage signals; and
an analog-to-digital converter connected to receive the reference voltage signal from the second piezoelectric transducer and configured to convert the reference voltage signal to digital reference voltage amplitude samples,
wherein the adaptive filter is further connected to receive the digital reference voltage amplitude samples from the analog-to-digital converter and determine the second amplitude in dependence on the digital reference voltage amplitude samples received from the analog-to-digital converter.

2. The system as recited in claim 1, wherein the adaptive filter comprises:
a variable-gain amplifier connected to receive digital unfiltered voltage amplitude samples and configured to output digital filtered voltage amplitude samples with a gain that is a function of a control signal; and
a second comparator connected to receive both the digital reference voltage amplitude samples and the filtered voltage amplitude samples and configured to output difference values representing respective differences between the digital reference voltage amplitude samples and the digital filtered voltage amplitude samples.

3. The system as recited in claim 2, wherein the adaptive filter further comprises an optimization algorithm configured to output the control signal to the variable-gain amplifier in dependence on the difference values output by the second comparator.

4. The system as recited in claim 3, wherein the adaptive filter further comprises a fast Fourier transform configured to convert the digital filtered voltage amplitude samples into the second voltage signal.

5. The system as recited in claim 1, further comprising a display device connected to the output of the first comparator and configured to display symbology representing the difference voltage signal.

6. The system as recited in claim 1, further comprising:
a temperature sensor thermally coupled to the structure and configured to output a digital temperature value;
voltage biasing circuitry connected to receive the temperature value from the temperature sensor and the voltage signal from the voltage source and send the digital voltage amplitude samples to the adaptive filter, wherein the voltage biasing circuitry is configured to convert the first voltage signal to the digital voltage amplitude samples based on the digital temperature value.

7. The system as recited in claim 6, wherein the temperature sensor comprises:
a resistance thermometer thermally coupled to the surface of the structure;
a Wheatstone bridge connected to the resistance thermometer and configured to output a DC voltage signal representing a resistance value of the resistance thermometer; and
a voltage sensor connected to receive the DC voltage signal from the Wheatstone bridge and configured to convert the DC voltage signal to the digital temperature value.

8. The system as recited in claim 7, wherein the voltage biasing circuit is connected to receive the digital temperature value from the voltage sensor and configured to adjust a bias voltage of the voltage signal sent to the reference and test piezoelectric actuators in dependence on the digital temperature value.

9. A structural health monitoring system comprising:
a structure having a surface;
first and second piezoelectric transducers arranged on the surface in a first pitch-catch configuration;
third and fourth piezoelectric transducers arranged on the surface in a second pitch-catch configuration;
a voltage source configured to generate a first voltage signal representing an uncompensated waveform having a first amplitude;
voltage biasing circuitry configured to convert the first voltage signal to digital voltage amplitude samples;
an adaptive filter configured to adaptively filter the digital voltage amplitude samples and output a second voltage signal representing a second waveform having a second amplitude different than the first amplitude;
a first comparator connected to receive reference and test voltage signals from the second and fourth piezoelectric transducers respectively and configured to output a difference voltage signal representing differences between the reference and test voltage signals; and
an analog-to-digital converter connected to receive the reference voltage signal from the second piezoelectric transducer and configured to convert the reference voltage signal to digital reference voltage amplitude samples, wherein:
the adaptive filter is further connected to receive the digital reference voltage amplitude samples from the analog-to-digital converter and further configured to output the second voltage signal representing the compensated waveform in dependence on the digital reference voltage amplitude samples received from the analog-to-digital converter;
the first and third piezoelectric transducers are connected to receive the second voltage signal from the adaptive filter and respectively configured to generate reference and test guided waves in first and second portions of the structure in response to receipt of the second voltage signal;
the second piezoelectric transducer is configured to sense a first one of the reference and test guided waves and output the reference voltage signal having a characteristic dependent on the first one of the reference and test guide waves; and
the fourth piezoelectric transducer is configured to sense a second one of the reference and test guided waves and output the test voltage signal having a characteristic dependent on the second one of the reference and test guided waves.

10. The system as recited in claim 9, wherein the adaptive filter comprises:
a variable-gain amplifier connected to receive digital unfiltered voltage amplitude samples and configured to output digital filtered voltage amplitude samples with a gain that is a function of a control signal; and
a second comparator connected to receive both the digital reference voltage amplitude samples and the filtered voltage amplitude samples and configured to output difference values representing respective differences between the digital reference voltage amplitude samples and the digital filtered voltage amplitude samples.

11. The system as recited in claim 10, wherein the adaptive filter further comprises an optimization algorithm configured to output the control signal to the variable-gain amplifier in dependence on the difference values output by the second comparator.

12. The system as recited in claim 11, wherein the adaptive filter further comprises a fast Fourier transform configured to convert the digital filtered voltage amplitude samples into the second voltage signal.

13. The system as recited in claim 9, further comprising a display device connected to the output of the first comparator and configured to display symbology representing the difference voltage signal.

14. The system as recited in claim 9, further comprising a temperature sensor thermally coupled to the structure and configured to output a digital temperature value, wherein the voltage biasing circuitry is connected to receive the temperature value from the temperature sensor and configured to output digital voltage amplitude samples which are dependent on the digital temperature value.

15. The system as recited in claim 14, wherein the temperature sensor comprises:
a resistance thermometer thermally coupled to the surface of the structure;
a Wheatstone bridge connected to the resistance thermometer and configured to output a DC voltage signal representing a resistance value of the resistance thermometer; and
a voltage sensor connected to receive the DC voltage signal from the Wheatstone bridge and configured to convert the DC voltage signal to the digital temperature value.

16. The system as recited in claim 15, wherein the voltage biasing circuit is connected to receive the digital temperature value from the voltage sensor and configured to adjust a bias voltage of the voltage signal sent to the reference and test piezoelectric actuators in dependence on the digital temperature value.

17. A method for detecting an anomaly in a structure, the method comprising:
(a) sending a first voltage signal having a first amplitude to a reference piezoelectric actuator which is acoustically coupled to generate a guided wave in a structure in response to receipt of the first voltage signal;
(b) receiving a reference voltage signal from a reference piezoelectric receiver which is acoustically coupled to detect the guided wave generated by the reference piezoelectric actuator in response to sending the first voltage signal;
(c) determining a second amplitude which is optimized to compensate for nonlinear behavior of the reference piezoelectric actuator and reference piezoelectric receiver based on the reference voltage signal;
(d) concurrently sending a second voltage signal having the second amplitude to the reference piezoelectric actuator and to a test piezoelectric actuator which is acoustically coupled to generate a guided wave in the structure in response to receipt of the second voltage signal;
(e) concurrently receiving reference and test voltage signals from reference and test piezoelectric receivers in response to sending the second voltage signal;
(f) outputting a difference voltage signal representing differences between the reference and test voltage signals received in response to sending the second voltage signal; and
(g) recording data representing the difference voltage signal in a non-transitory tangible computer-readable storage medium,
wherein steps (a) through (d) are performed by an adaptive filter.

18. The method as recited in claim 17, wherein step (c) is performed by an optimization algorithm of the adaptive filter that is configured to adjust an amplitude of the second voltage signal sent to the reference and test piezoelectric actuators to compensate for variation in piezoelectric transducer performance due to an environmental factor.

19. The method as recited in claim 18, wherein the environmental factor is a temperature.

20. The method as recited in claim 19, further comprising:
measuring the temperature of the structure; and
adjusting a bias voltage of the voltage signal sent to the reference and test piezoelectric actuators in dependence on the measured temperature.

* * * * *